US006362881B1

(12) United States Patent
Pickering et al.

(10) Patent No.: US 6,362,881 B1
(45) Date of Patent: Mar. 26, 2002

(54) IN-SITU MONITORING OF ELECTRICAL PROPERTIES BY ELLIPSOMETRY

(75) Inventors: Christopher Pickering; Roger T Carline, both of Malvern (GB)

(73) Assignee: The Secretary of State for Defence, Farnborough (GB)

( * ) Notice: Subject to any disclaimer, the term of this patent is extended or adjusted under 35 U.S.C. 154(b) by 0 days.

(21) Appl. No.: 09/297,819

(22) PCT Filed: Dec. 18, 1997

(86) PCT No.: PCT/GB97/03367

§ 371 Date: May 10, 1999

§ 102(e) Date: May 10, 1999

(87) PCT Pub. No.: WO98/28606

PCT Pub. Date: Jul. 2, 1998

(30) Foreign Application Priority Data

Dec. 23, 1996 (GB) .............................. 9626765

(51) Int. Cl.[7] .................................................. G01J 4/00
(52) U.S. Cl. ..................................................... 356/369
(58) Field of Search ............................... 356/364, 365, 356/369, 432; 250/225

(56) References Cited

U.S. PATENT DOCUMENTS 4,446,719 A * 5/1984 Lambert ..................... 250/341

5,255,071 A * 10/1993 Pollak et al. ................ 356/432
5,287,169 A * 2/1994 Pollak et al. ................ 356/432
5,501,637 A   3/1996 Duncan et al. ............. 374/126
5,536,936 A * 7/1996 Drevillon et al. ........... 356/432

FOREIGN PATENT DOCUMENTS

EP   0 409 271 A   1/1991
FR   2 714 970 A   7/1995

OTHER PUBLICATIONS

Xiong Y –M et al: "Photoellipsometry Studies of Delta–Doped GAAS and Modulation–Doped ALGAAS/GAAS Heterojunction Structures" Thin Solid Films, vol. 270, No. 1/02, Dec. 1, 1995, pp. 300–306, XP000595237, see the whole document.

* cited by examiner

Primary Examiner—F. L. Evans
Assistant Examiner—Zandra V. Smith
(74) Attorney, Agent, or Firm—Nixon & Vanderhye P.C.

(57) ABSTRACT

A method of monitoring material parameters of a sample (4) (for example electrical properties of a semiconductor) during processing (for example during manufacture) which uses ellipsometric techniques to study the changes induced in the ellipsometric spectra of the material, by modulation of the internal electric field of the material, and determining from these changes the material parameters of interest The means of modulation can be a source of electromagnetic radiation, for example a laser (8). The ellipsometer used may include an array of photodetectors. The process allows the real time monitoring of the process under examination.

12 Claims, 11 Drawing Sheets

IN-SITU MONITORING OF ELECTRICAL PROPERTIES BY ELLIPSOMETRY

BACKGROUND OF THE INVENTION

1. Field of the Invention

Numerous areas of the electronics industry require electronic materials and devices with precisely specified electrical properties. Material composition and strain are important parameters in determining a materials electronic properties, whilst accurate positioning and magnitude of dopants and interfaces in a device is essential to obtain optimum performance. Achieving these specifications is non-trivial and monitoring of electrical and material information, as well as process parameters such as wafer temperature, during fabrication and non-destructive testing are desired to optin se material, device and system performance.

2. Discussion of Prior Art

The largest areas of electronic production centres on the use of semiconductors. Within the next ten years semiconductor processing concepts are likely to undergo a fundamental change. Increasing demands for reduced dimensions and increased complexity will lead to enormous costs for conventional fabrication plants, which will become viable only for high volume markets. Low volume application specific devices and ICs will require more flexible, lower cost manufacturing approaches. Single-wafer processors, which rely for flexibility and control of specification on intelligent in-situ optical sensors, are seen as central to this development Feedback control of primary process parameters will need to be implemented in response to desired wafer parameters which will therefore need to be measured rapidly in-situ. Optical techniques such as reflectance[1] and Ellipsometry (including both single wavelength and Spectroscopic Ellipsometry[2] (SE)) are being developed to satisfy this role. Though they provide detailed information on the thickness and composition of a sample they are insensitive to electrical properties and this represents a major limitation in their use. Techniques which can provide electrical information in-situ and real-time have not been available. PSE is such a technique. Standard in-situ optical diagnostics can also be limited by their sensitivity to system variations (polariser speed in SE and light intensity in reflectance) which introduce errors in the calculated compositions and thicknesses. Errors are greater when monitoring thin layers where it becomes difficult to distinguish between the effects of thickness and composition on measured spectra.

An unambiguous determination of composition using a compatible technique which is insensitive to system variations would also simplify the interpretation of measured spectra to give reliable thickness information.

Photo-modulated ellipsometry provides such a determination being insensitive to both system variations and epilayer thickness effects (which complicate the interpretation of reflectance and ellipsometry data) in the samples. In-situ real-time measurement of temperature using SE is also prone to errors introduced by system variations and the presence of reflecting layers in a sample can introduce large errors in radiation measurements such as pyrometry. PSE provides a robust and rapid alternative method of measuring temperature.

Photo-modulated ellipsometry is a relatively new characterisation technique based on the high precision and electric field sensitivity of a photomodulated measurement and the insensitivity to noise and drift provided by ellipsometry. Ellipsometry is based on the measurement of the change in phase and amplitude of a light beam reflected from the sample surface. The measured ellipsometry parameters, $\psi$ (amplitude ratio) and $\Delta$ (phase), can be related to the effective dielectric constant ($<\mathcal{E}>=<\mathcal{E}_1>+i.<\mathcal{E}_2>$) of the sample, often referred to as the pseudo-dielectric function for spectroscopic measurements. Complex analysis can provide the dielectric function of a single layer, $\mathcal{E}=\mathcal{E}_1+i.\mathcal{E}_2$, in a multilayer sample or of a surface layer, which is important for monitoring of dynamic processes such as epitaxial growth where the surface is changing. The dielectric function can provide information on material temperature, composition and strain, but little direct information relating to electric fields. Photomodulated spectroscopies, such as photoreflectance (PR), use a laser beam to modulate surface and interface electric fields. Derivative spectra, of the reflected amplitude only, are obtained due to a field induced change in the localised dielectric function of the sample. PSE uses laser modulation in the same way yielding derivative spectra of the SE parameters, $\psi$ and $\Delta$, and so $\Delta\mathcal{E}=\Delta\mathcal{E}_1+i.\Delta\mathcal{E}_2$ from each layer being modulated.

The similarity in origin of photo-modulated ellipsometry and PR signals allows techniques for the analysis of PR spectra to be adapted for use on PSE spectra. These are based on Apnes's third derivative approximation[3] which allows the derivative spectra to be fitted to provide critical point (CP) transitions energies in the material band structure amplitudes and broadnesses, which can then be related to material composition, strain, temperature and material quality. Observation of Franz-Keldish oscillations in the spectra can also be used to evaluate electric fields.

Modulated ellipsometry measurements have been reported as early as the late 1960s[4,5] on metal samples, and using an electrolyte for modulation. Measurements were also made on Ge[6,7] but little has been reported in the literature until 1990 when photo-modulated spectroscopic ellipsometry was first reported[8]. Since then, several PSE measurements have been reported on III–V semiconductor structures using standard SE instruments[9-14].

PSE spectra were achieved using two different techniques. Both techniques used the point-by-point wavelength scans of the standard automated SE instruments. Xiong et al[11-13] measured SE parameters one wavelength at a time for two individual SE spectra, one with the laser on and one with the laser off. Dielectric function spectra were calculated from these parameters and spectra with the laser off subtracted from those with the laser on to give the $\Delta\mathcal{E}$. Both CP transition energies[13,14] and electric field[10-14] information were obtained from these spectra. Zettler et al[8-10] and Vanderhaghen et al[15] chopped the laser beam and used phase sensitive detection to record PSE parameters.

SUMMARY OF THE INVENTION

According to this invention, a method of monitoring material parameters, including electric field; composition; strain; temperature or surface topography, during processing of material, comprises the steps of modulating the internal electric field of the material monitoring the change spectra that said modulation induces, using a real-time ellipsometer, and relating said change spectra to any of said parameters. The processing referred to includes manufacture and other industrial processes intended to modify the properties of the material.

The real time ellipsometer may be of the single wavelength type or of the spectroscopic type.

The internal electric field of the sample may be modulated using an electron beam or a laser. In the latter case, the parameters may further include laser power and laser alignment.

BRIEF DESCRIPTION OF THE DRAWINGS

The invention will now be described with reference to the following figures of which.

DETAILED DISCUSSION OF PREFERRED EMBODIMENTS

In this section a description is given of the method used to obtain in-situ PSE spectra in times as short as 0.5 s. Such short acquisition times are consistent with that required for real-time process control in systems where typical growth rates of 1 monolayer/second are exhibited, such LPVPE growth of Si/SiGe.

First, a description of the experimental set-up and sample growth is given. Following this two measurements are described, one ex-situ (i.e. on a goniometer specifically designed for doing such measurements), and two in-situ (i.e. where the instrumentation used was brought to the sample) to demonstrate the proposed technique and its use.

Experimental Set-up

Rapid room-temperature PSE measurements on Si and SiGe/Si samples are described. The PSE measurement is based on use of a SOPRA MOSS OMA instrument to provide SE spectra. The PSE spectra are calculated as the difference between two SE spectra, one measured with laser illumination of the sample, and one without. PSE spectra obtained from samples located ex-situ, and in-situ in a growth reactor are presented. Both were measured using the same SE instrument.

Figure 1:
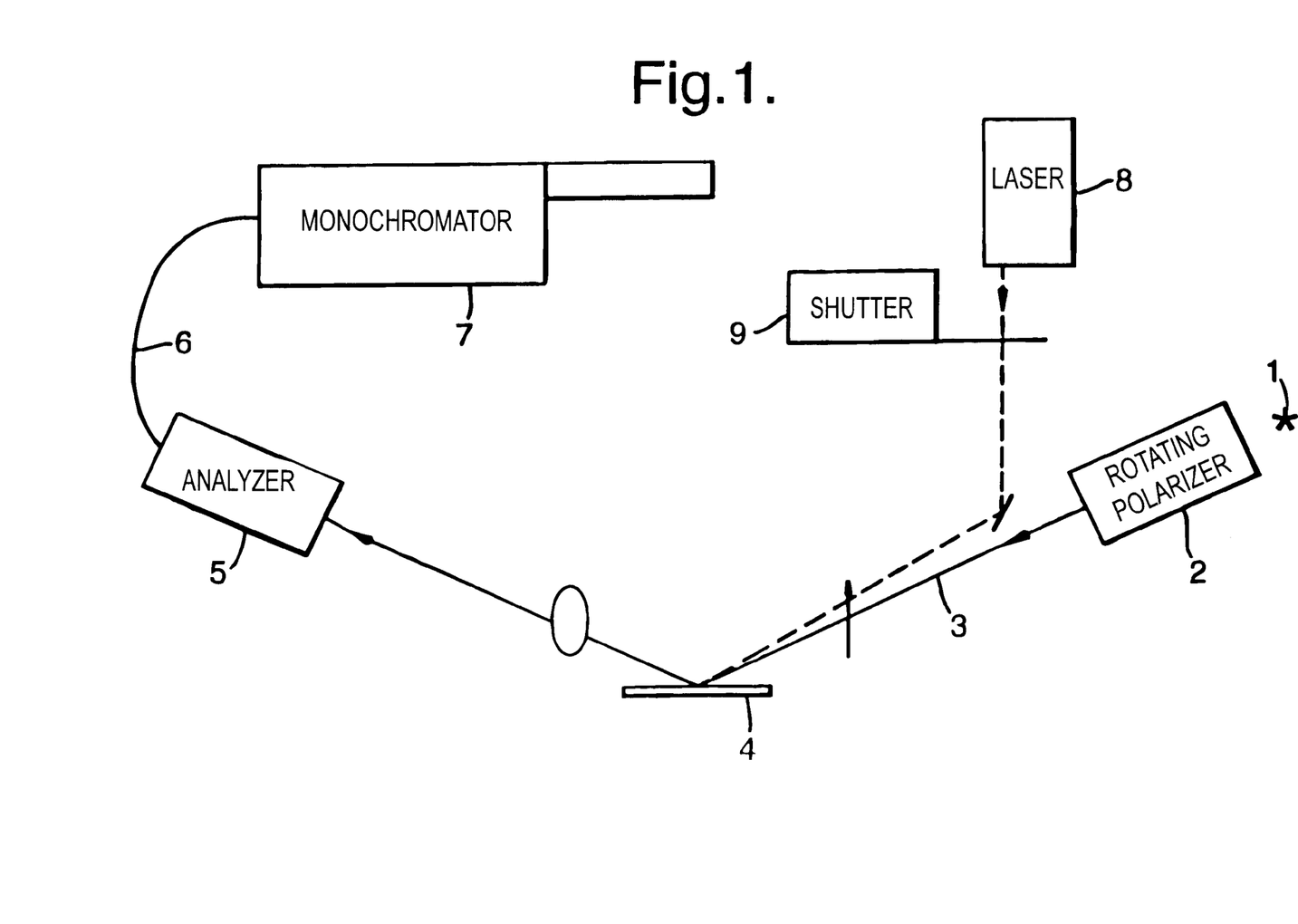
FIG. 1 shows a schematic representation of the apparatus used to obtain automated, real-time PSE measurements.

A schematic of the PSE set-up is shown in FIG. 1. Light from a Xe lamp 1 passed through a rotating polariser 2 provides the probe beam 3 which is reflected from the sample 4 through a fixed analyser 5 into an optical fibre 6. The optical fibre passes the light into a prism monochromator 7 in which the dispersed light is detected by a 1024 pixel diode array. The signal is averaged over groups of pixels. The available groupings includes 4 pixels, which is used ex-situ, and 8 pixels which is in-situ. This gives improved signal/noise ratio but reduced spectral resolution for the in-situ spectra. Data acquisition and processing is fully automated to give the experimental tan $\psi$, cos $\Delta$ spectra. A laser 8 is shuttered between SE measurements (by means of shutter 9) to give modulated and unmodulated SE spectra. An $Ar^+$ ion laser is used for in-situ measurements whilst a HeNe laser is used for measurements made ex-situ. In both cases the laser power at the sample is 10 mW unless stated otherwise. In-situ measurements are made with the sample housed in a low pressure stainless steel vapour phase epitaxy chamber which and with an angle of incidence of 70°. Ex-situ measurements were made at 75° with the sample and SE instrument mounted on a variable angle goniometer. Both angles of incidence are close to the Brewster angle of Si, considered most sensitive for SE.

Theory

The method of analysis used to illustrate the invention is based on Aspne's low field theory[3]. This states that the change in dielectric function ($\Delta\epsilon=\Delta\epsilon_1+i.\Delta\epsilon_2$) in the region of a direct critical point transition, $E_g$, brought about by a change in electric field, F, is given by equation 1, $$\Delta(\varepsilon_1 + i \cdot \varepsilon_2) = (\hbar\theta)^3 \frac{d^3}{dE^3}(\varepsilon_1(E - E_g, \Gamma) + i \cdot \varepsilon_2(E - E_g, \Gamma)) \quad (1)$$

where E is a spectral energy and $\Gamma$ is a broadness. $(\eta\theta)^3$ is the electro-optic energy given by, $$(\hbar\theta)^3 = \frac{q^2\hbar^2 F^2}{2\mu} \quad (2)$$

where $\mu$ is the interband effective mass in the direction of the field and q and $\eta$ have their usual meanings. Comparing equations 1 and 2 it can be seen that, if the photo-modulated ellipsometry signal ($\Delta\epsilon$), the third derivative of the dielectric constant and the effective mass are known, the electric field can be evaluated. Comparison between third derivative dielectric function spectra (DSE spectra) and theoretically evaluated ($\Delta\epsilon$) spectra has been reported as a method of predicting $\mu^{17}$, however, use of experimental photo-modulated ellipsometry spectra to obtain F is not known in the prior art. The right hand side of equation 1 can be fitted using a variety of lineshapes and functions[3]. Typically F, a phase, an amplitude and a CP energy gap, $E_g$, are obtained as fitting parameters. The strain, composition and temperature of a material can be predicted from the values of $E_g$ obtained from one or more CP transitions.

PSE Measurement and Analysis

Field Measurements Without FKO Oscillations

Figure 2A:
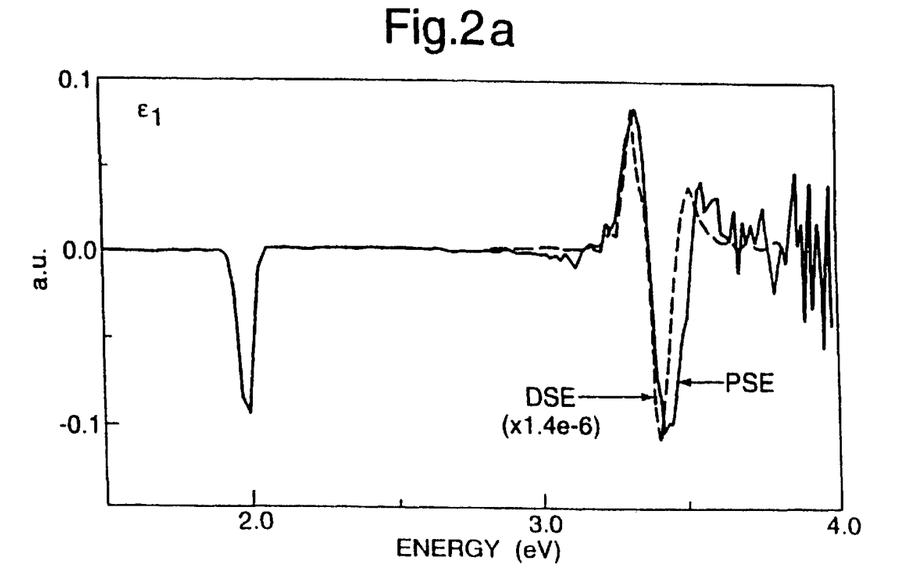
FIG. 2 shows a comparison of PSE spectra, measured ex-situ on a Si sample at room temperature, with the third differential of the reference dielectric function spectra of $Si^{18}$.
Figure 2B:
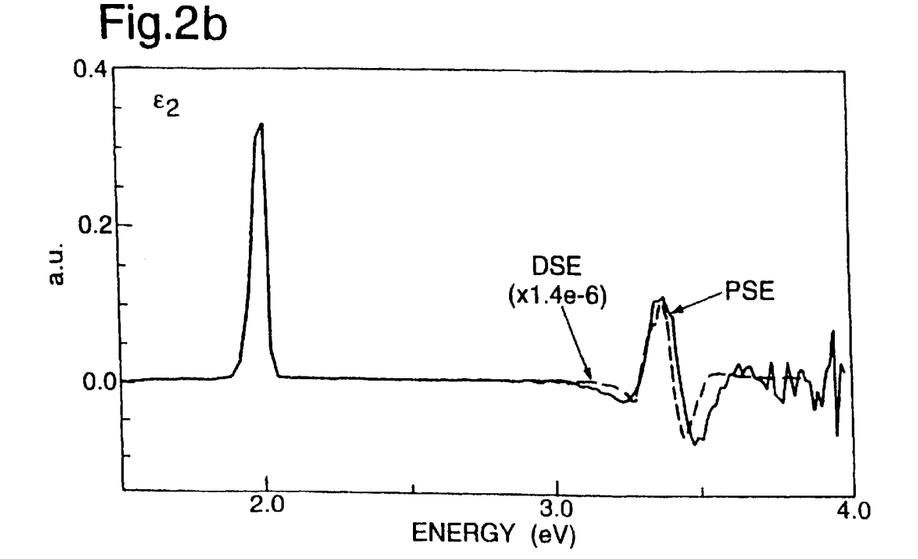

FIG. 2 shows the ex-situ room temperature PSE measurements ($\Delta\epsilon_1$ and $\Delta\epsilon_2$) obtained using a 4 pixel grouping from a sample which consisted of an undoped layer of Si grown epitaxial on a $p^+$ Si substrate. The integration time was 200 s per SE spectrum (400 s for a PSE measurement).

Figure 3A:
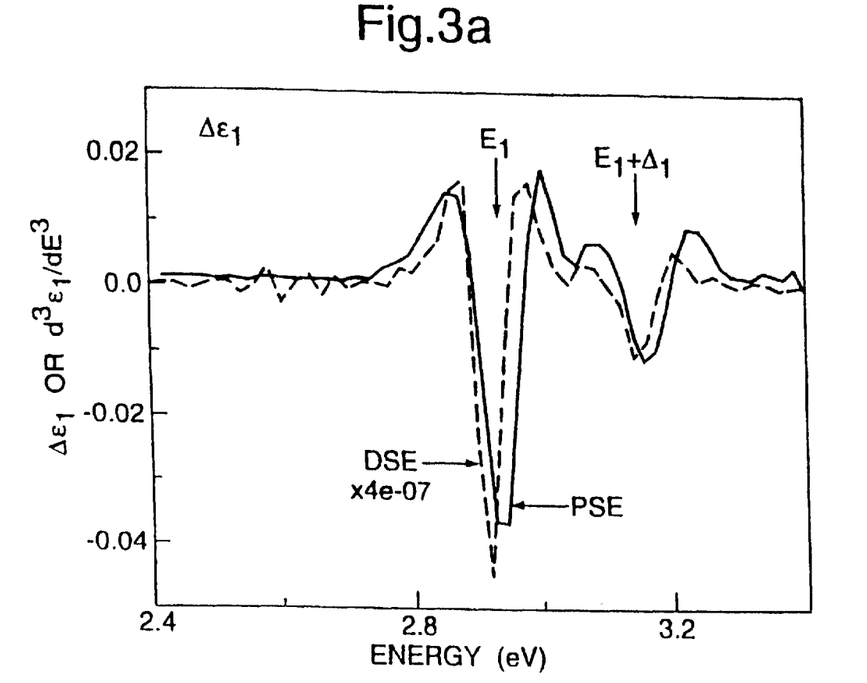
FIG. 3 shows a comparison of PSE spectra measured ex-situ on a GaAs sample at room temperature with the third differential of the reference dielectric function spectra of $GaAs^{18}$.
Figure 3B:
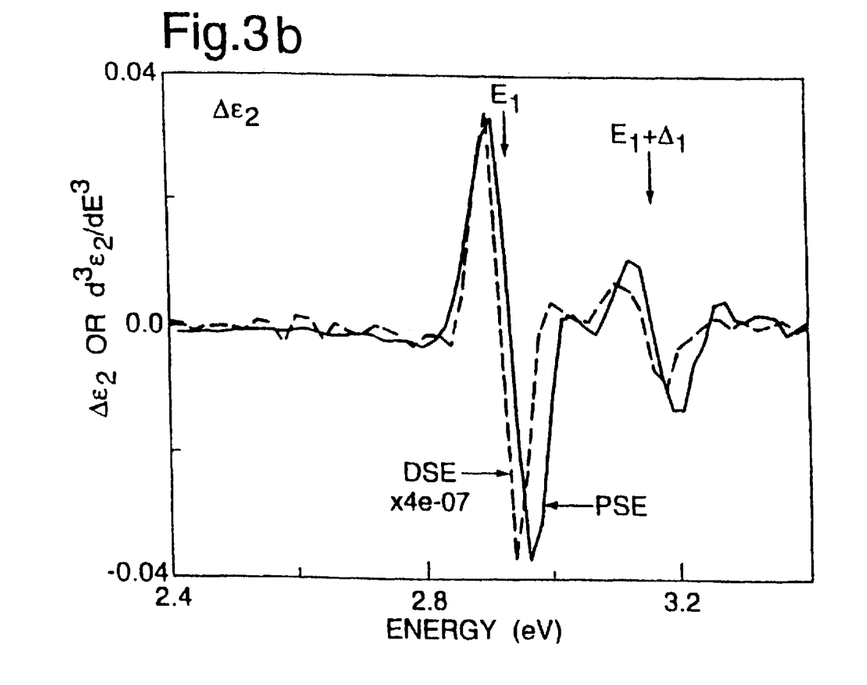

Spectra of the third derivative of the dielectric function spectra of $Si^{18}$, $d^3(\epsilon_{Si})/dE^3$, where $\epsilon_{Si}=\epsilon_{1(Si)}+i\epsilon_{2(Si)}$, which have been scaled to match the PSE are also shown in the range 3.0–3.8 eV. The origin of the Lorentzian feature at ~3.4 eV seen in both spectra is the dominant $E_0'$ critical point transition. As can be seen, the spectral lineshapes compare well. Use of equations 1 and 2 gives an electric field $$F = \sqrt{\frac{1.4 \times 10^{-6} \cdot n\mu}{q^2 \hbar^2}} \qquad (3)$$

where n is a constant to allow for the degeneracy of the minima with effective mass $\mu$. For Si, and other situations where FKO oscillations are not seen, relative changes in electric field can be monitored by analysing PSE measurement using this equation. Absolute electric fields could be evaluated once correct values of $\mu$ and n are established and provided effects such as exchange-and-correlation and non-unifom fields, which can modify the PSE spectra, are quantified, or shown not to be significant. The peak in the PSE spectra at ~2 eV is caused by non-specular laser light being scattered from the sample into the SE detector and the increase in the experimental noise on the PSE spectra above 3.6 eV is due to a reduction in the intensity of the SE probe beam. FIG. 3 shows the ex-situ room temperature PSE ($\Delta\epsilon_1$ and $\Delta\epsilon_2$) obtained from a undoped GaAs layer on an $n^+$ GaAs substrate measured using the same experimental conditions as described for FIG. 2 above. Spectra of the third derivative of the dielectric function spectra of $GaAs^{18}$ which have been scaled to match the PSE are also shown in the range 2.4–3.4 eV. The origin of the Lorentzian feature at ~2.9 eV seen in both spectra is the dominant $E_1$ critical point transition in whilst that at ~3.15 eV corresponds to the $E_1+\Delta_1$ critical point transition. Again, the spectral lineshapes compare well.

Sensitivity to Changing Fields

Figure 4:
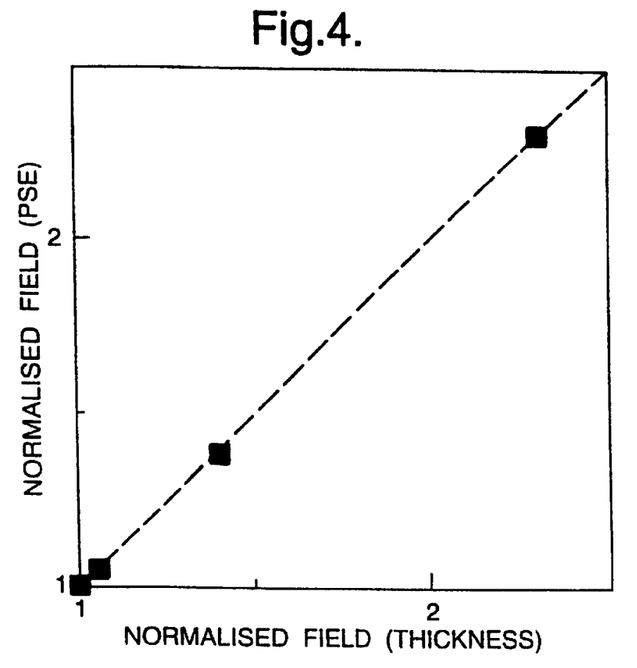
FIG. 4 shows a comparison of the normalised variation of electric field calculated from PSE measurements at four positions on a 100 mm $\{Si(cap)/Si_{0.79}Ge_{0.21}/Si(p^+)/Si(100)\}$ sample with the field variation expected from a thickness variation in the total $Si(cap)+Si_{0.79}Ge_{0.21}$ thickness calculated from spectroscopic ellipsometry measurements at the same positions.

For a large range of in-situ real-time applications it may be sufficient that the PSE should provide relative field values. An illustration of the results that can be obtained is shown in FIG. 4. This shows the electric field calculated using PSE spectra recorded at positions with different Si cap thickness 10 mm apart along a radius of a 100 mm {Si/$Si_{0.79}Ge_{0.21}$/Si($p^+$)/Si(100)} sample wafer. These are compared with the variation expected from thicknesses evaluated using scanning spectroscopic ellipsometry (SE) spectra obtained at the same positions. Both sets of results are normalised to the measurement made nearest the wafer centre. A constant thickness and alloy composition of $Si_{0.79}Ge_{0.21}$ epilayer was found from the scanning SE at all four positions whilst cap thicknesses varied from 31 nm to 18.5 nm. The radial reduction in Si cap thickness starting 20 mm from the wafer centre means the electric field across the insulating Si cap and $Si_{0.79}Ge_{0.21}$ epilayers will increase towards the wafer edge, as is illustrated in FIG. 4. The agreement in field variation evaluated from SE and PSE is excellent.

Field Measurements Using FKO Oscillations

Figure 5:
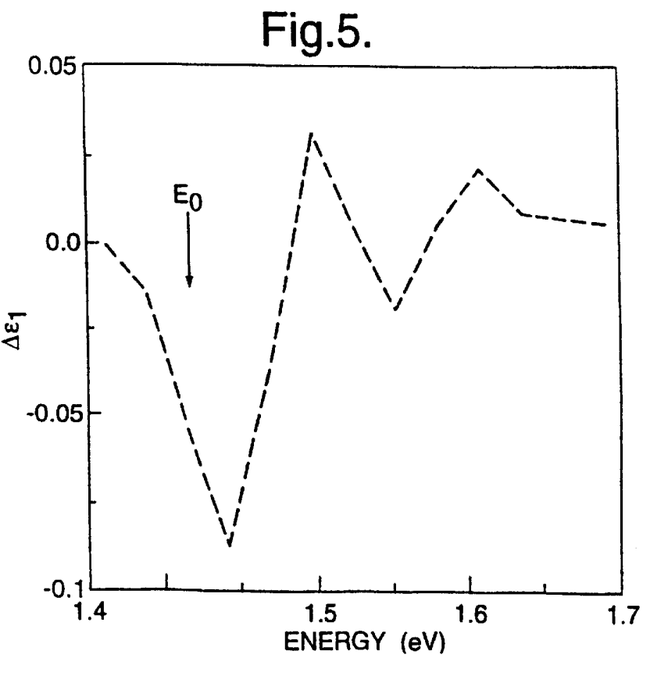
FIG. 5 shows FKO oscillations in the real part of the PSE measurement for a GaAs sample.

Electric fields are routinely obtained from modulation spectra where FKO are observed. One approach is to calculate the electro-optic energy from the position of oscillation extrema. This is true of the PSE spectra discussed here also. FIG. 5 shows that FKO can be observed using the PSE measurement described here. The data is from a different spectral range of the PSE measurement of the GaAs sample described above. The FKO can be seen above the $E_0$ critical point of the GaAs sample.

In-situ Measurements

Figure 6A:
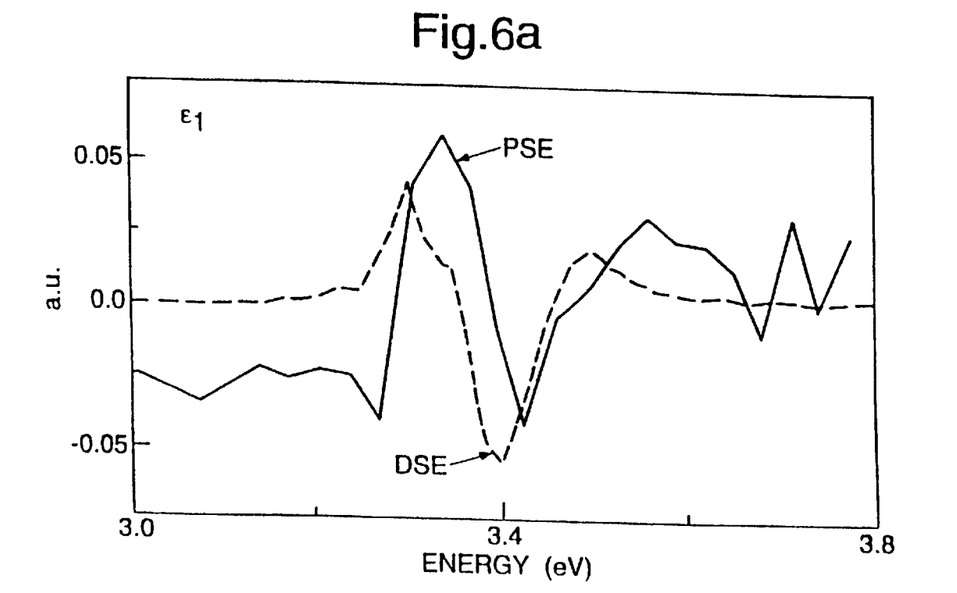
FIGS. 6 and 7 show comparisons of PSE spectra, measured in-situ in 60s and 120s respectively, on a $p^+$ Si substrate at room temperature, with the third differential of the reference dielectric function spectra of Si.
Figure 6B:
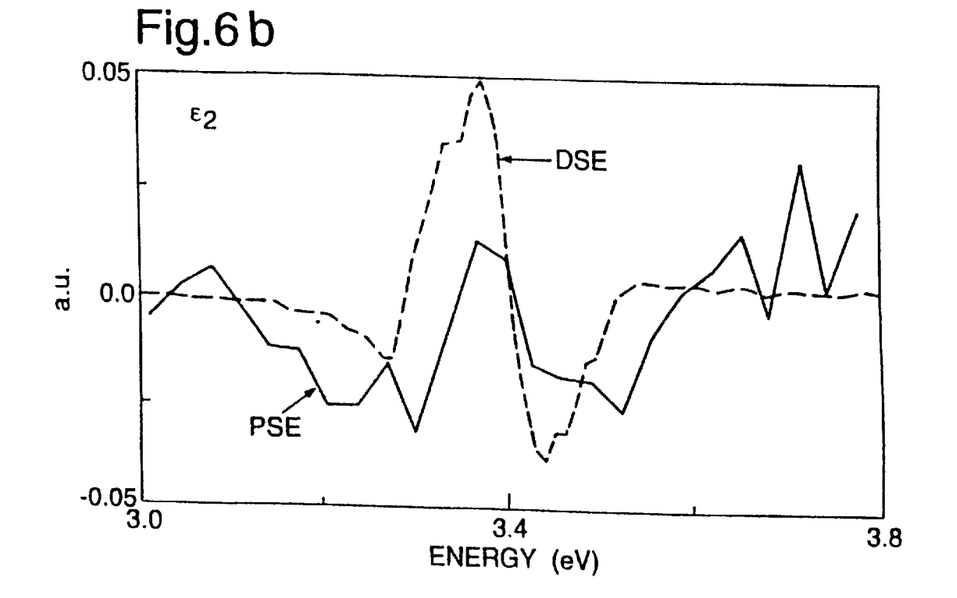
Figure 7A:
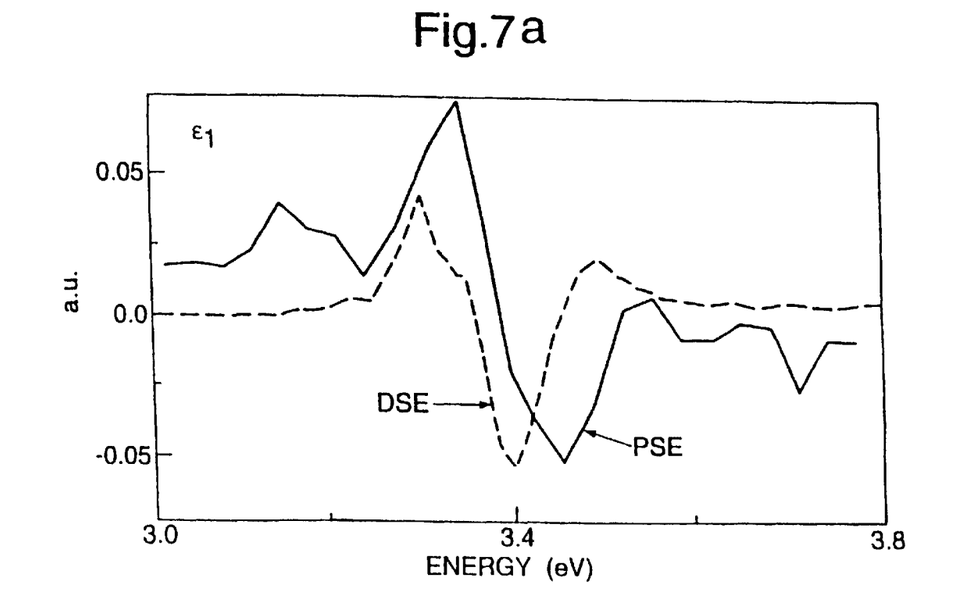
Figure 7B:
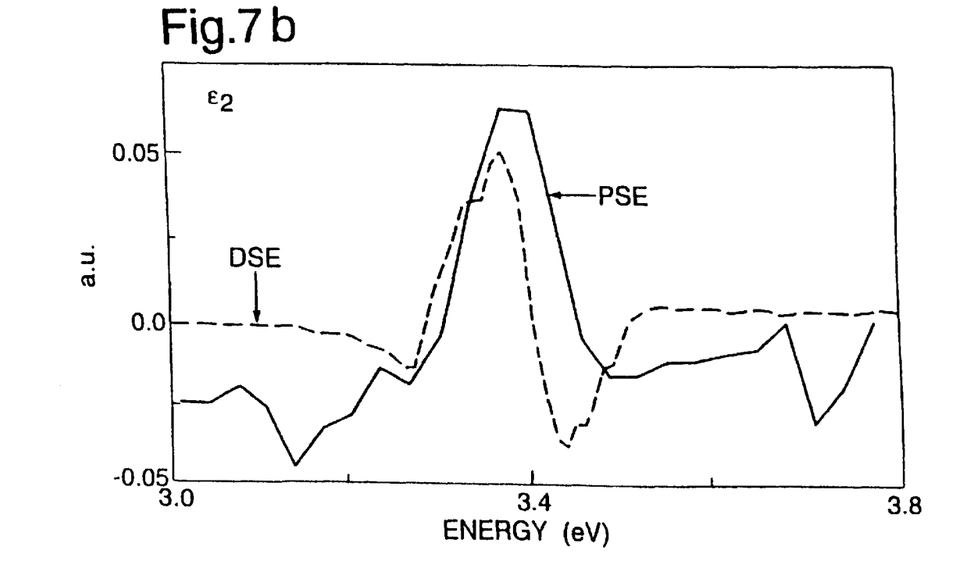
Figure 8A:
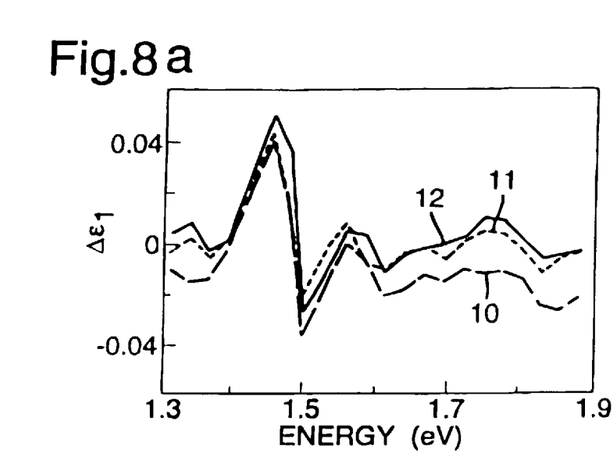
FIG. 8 shows a comparison of spectra, measured ex-situ in 0.5 s, 1 s and 60 s, on a GaAs sample at room temperature.
Figure 8B:
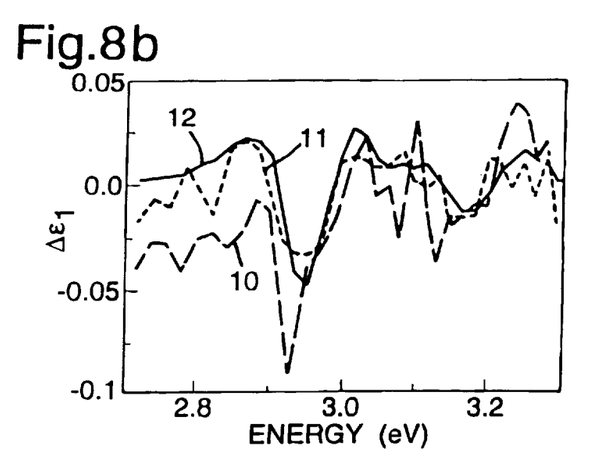
Figure 8C:
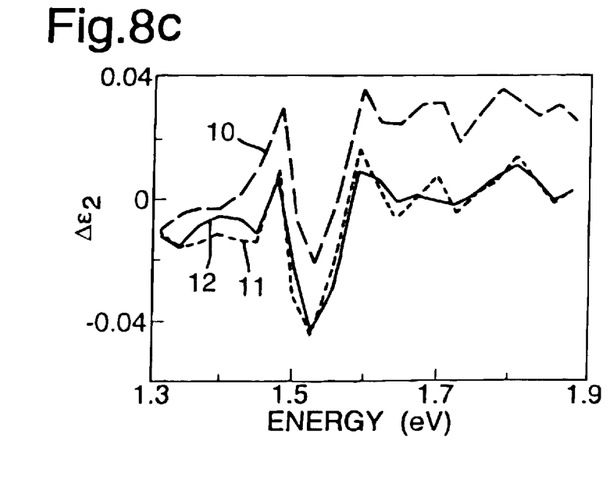
Figure 8D:
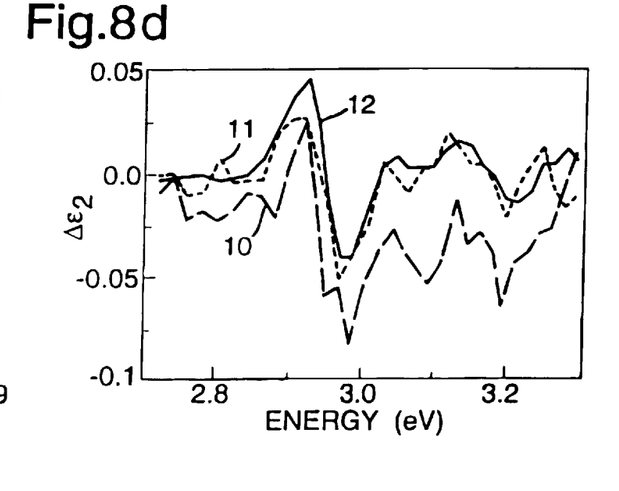

FIGS. 6 and 7 compare DSE spectra for Si with in-situ room temperature PSE measurements made on $p^+$ Si substrates using an 8 pixel grouping. The PSE spectra of FIG. 3 were obtained in 60 s and those in FIG. 4 were obtained immediately afterwards but in 120 s. An unintentional offset caused by drift in the speed of the rotating polariser is seen in the PSE spectra which should have approximately zero amplitude at 3 and 3.8 eV. This error was not seen in the ex-situ PSE measurements, such as that in FIG. 2. The instrument used to obtain the ex-situ measurements had a digitally controlled polariser motor whereas that used to obtain the in-situ measurements had an analogue controlled motor. The improvement in signal/noise for longer accession time is apparent in comparing FIGS. 6 and 7. Also, the PSE spectra in FIGS. 6 and 7 are broader than that shown in FIG. 2 due to the reduced resolution obtained when using a larger pixel grouping. The DSE spectra were scaled by 7e–07 and 8e–08, respectively, to match the PSE. Comparison of the two figures demonstrates consistency in scale and lineshape of sequential PSE spectra obtained in-situ.

Rapid Measurements

FIG. 8 compares three room temperature PSE spectra measured using a 4 pixel grouping and integration times of 0.5 s 10, 1 s 11 and 60 s 12 on a sample consisting of an undoped GaAs epilayer on an $n^+$ GaAs substrate. Lorentzian features corresponding to the $E_0$ (1.4–1.5 eV) $E_1$ (~2.9 eV) CP transitions are evident in all three spectra The peak-to-peak amplitude and energy position of the Lorentzians in the three spectra are the same to within the error represented by the experimental noise on the PSE spectra. The $E_1+\Delta_1$ (~3.2 eV) CPs are only evident above the noise in the 1 s and 60 s spectra. That spectra are observed and show stable CP position and magnitude demonstrates the ability of the technique to provide near real-time monitoring of field composition, strain and temperature during processes which occur on a 0.5 s time-scale, such as epitaxial growth.

After the first laser-on then laser-off measurement, which takes two SE scans, and so twice the SE scan time to acquire a single PSE spectra, continuous monitoring using SE spectra with the laser alternately on then off gives a PSE spectra after each SE scan by subtracting the last SE scan (alternate PSE spectra will have the opposite sign). Improvements in system stability and signal/noise will be obtained with the advent of the next generation of RTSE instruments making sub 1 s PSE repeat time a viable option.

Stability of the PSE Measurement

Figure 9A:
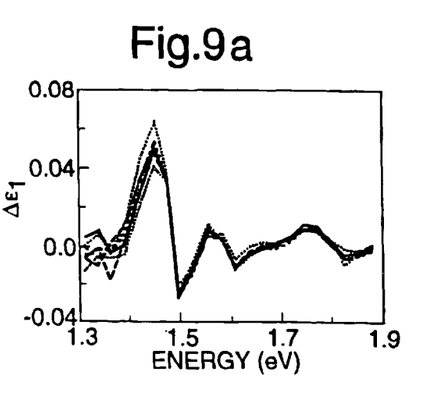
FIG. 9 shows a comparison of PSE spectra, measured ex-situ in 60 s on a GaAs sample at room temperature, along with the corresponding SE spectra measured without laser illumination.
Figure 9B:
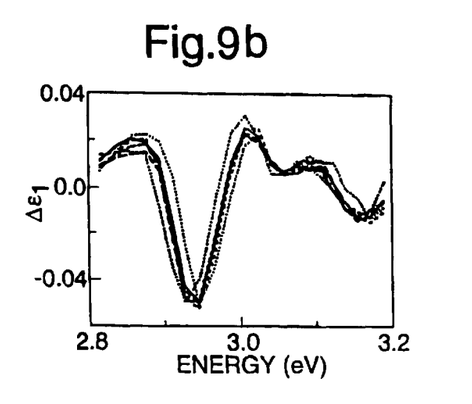
Figure 9C:
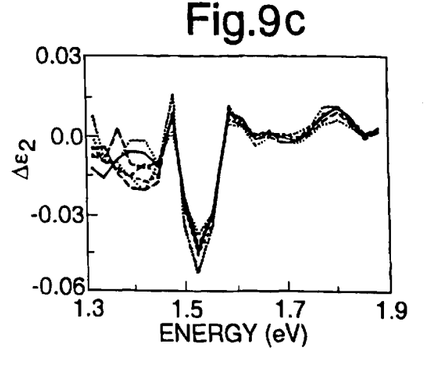
Figure 9D:
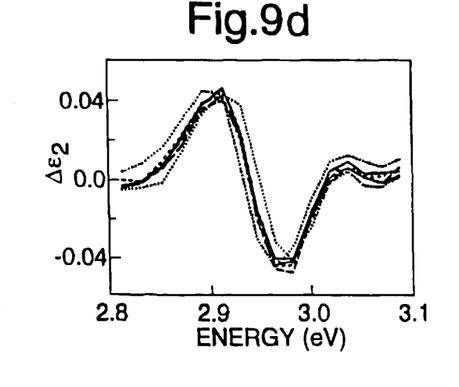
Figure 9E:
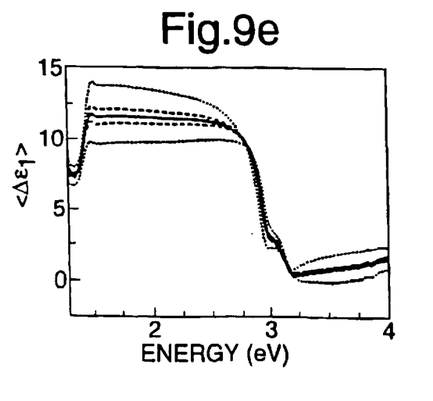
Figure 9F:
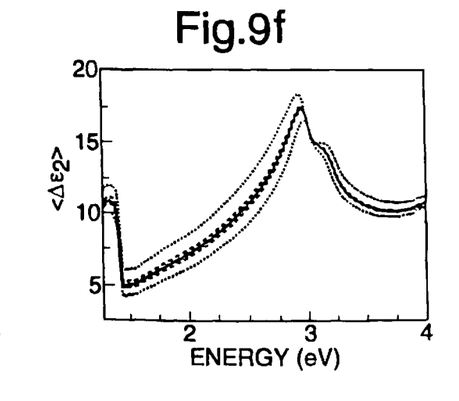

FIGS. 9a, 9b, 9c and 9d shows a comparison of seven room temperature PSE spectra measured with integration times of 60 s with a 4 pixel grouping on a sample consisting of an undoped GaAs epilayer on an $n^+$ GaAs substrate. The PSE spectra were recorded using SE measurements made with different calibrations. The SE measurements made without laser illumination are shown in FIGS. 9e and 6f. The SOPRA OMA measurement uses three calibration parameters, $A_0$ (value of the analyser at the plane of incidence), $\alpha P$ and $\beta P$ (zero crossing and gradient to allow for the rotation of the polariser during a measurement). Each was varied by +/–10% to give a pair of curves with the same line type in FIG. 9. This represents a larger variation than would be expected from normal system variations which is evident from the large difference in the measured SE spectra in FIGS. 9d and 9e. The solid curves were measured with the correct (measured) calibration. As can be seen there is no appreciable difference in the PSE spectra for variations in the parameters $A_0$ and $\alpha P$. This insensitivity is especially important in the case of $A_0$ which can vary during a monitoring run due to changes in sample position/alignment caused by heating etc. A noticeable variation in the position of the PSE peaks in FIGS. 9b and 9d suggest that the PSE spectra are more sensitive to βP. The shift in energy position of the absorption edge and peaks seen in the corresponding SE spectra would introduce a large error in the composition, strain or temperature derived from an analysis of the SE spectra of an alloy such as strained $In_xGa_{1-x}As$ or $Si_xGe_{1-x}$. (e.g. the shift in absorption edge is as large as 0.38 eV corresponding to a change in x of >0.25[19,20] for both these alloys).

The variation in CP position seen in the PSE spectra however would be seen as a variation in alloy composition of ≦0.01[19,20], emphasising the insensitivity of the PSE technique to system variations which effect the SE calibration.

PSE Sensitivity to Laser Power

Figure 10A:
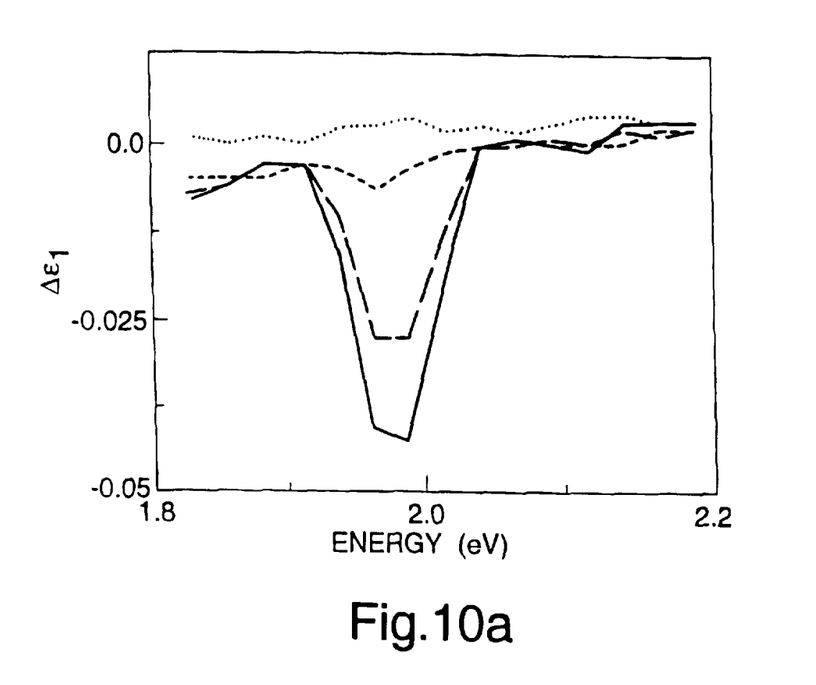
FIG. 10 shows PSE spectra in the wavelength range of the excited HeNe laser line for laser powers (in mW) of 3.2, 1.3, 0.3 and 0.01
Figure 10B:
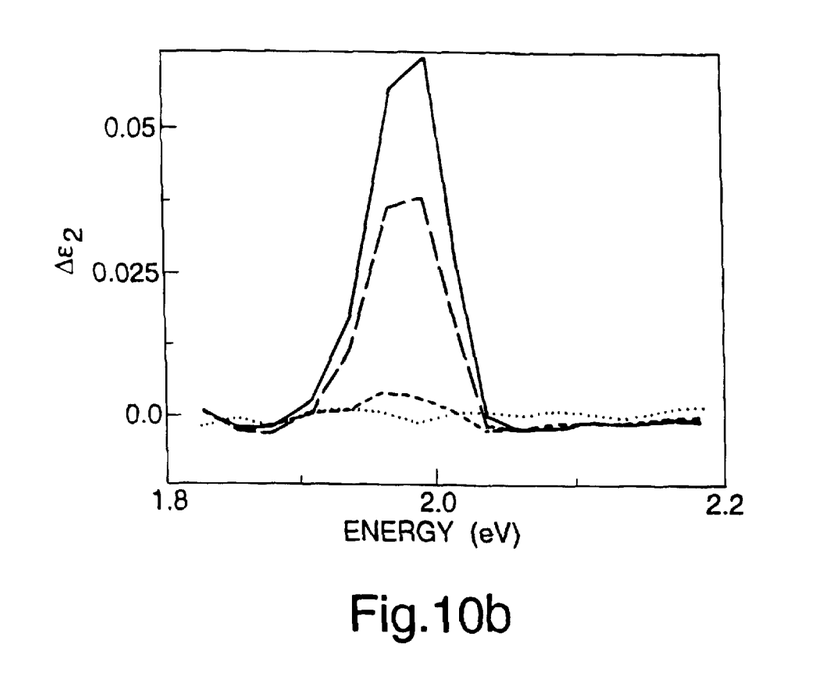

FIG. 10 compares a restricted wavelength region of four room temperature PSE spectra measures using a 4 pixel grouping and integration times of 200 s on a sample consisting of an undoped GaAs epilayer on an $n^+$ GaAs substrate. The spectra are measured with different intensities of HeNe laser used to modulate the sample for the PSE measurement. It is to be noted that the laser alignment is such that the laser light being detected is due to scattering of laser light from the wafer rather than the specular laser beam. As can be seen the intensity of the peak in the PSE spectra varies monotonically with laser power. The intensity of this peak can therefore be used as a monitor of effects which vary the amount of scattered laser light entering the SE detector. These could include variations in the laser power, variations in the laser/sample alignment or variations in the surface topography of the sample.

Figure 11:
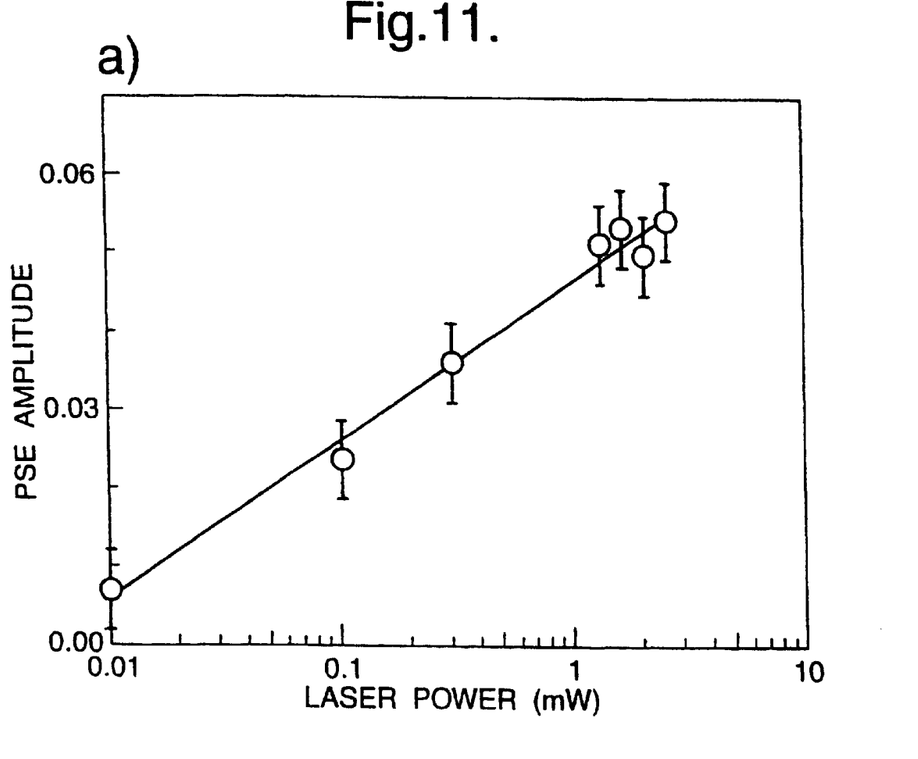
FIG. 11 shows the variation in amplitude of differential structure in the PSE spectra as a function of modulating laser power for GaAs and Si and FIG. 12 shows a PSE specimen obtained from an $Si/Si_{1-x}Ge_x/Si(P^+)$ sample, for which x=0.2, and the variation in position of differential structure in the PSE spectra as the composition, x, varies.

FIG. 11 compares the amplitudes of differential structure associated with the $E_1$ critical point in the PSE spectra of GaAs. From this variation the laser power may be measured. Above 2 mW of laser power the amplitude saturates and information on the laser power is not available from this experiment.

PSE Sensitivity to Composition

Figure 12A:
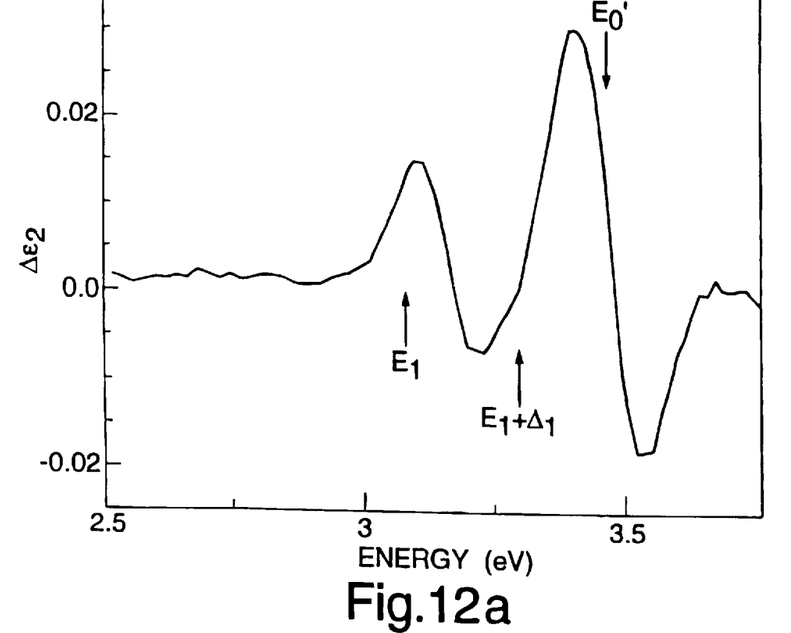
Figure 12B:
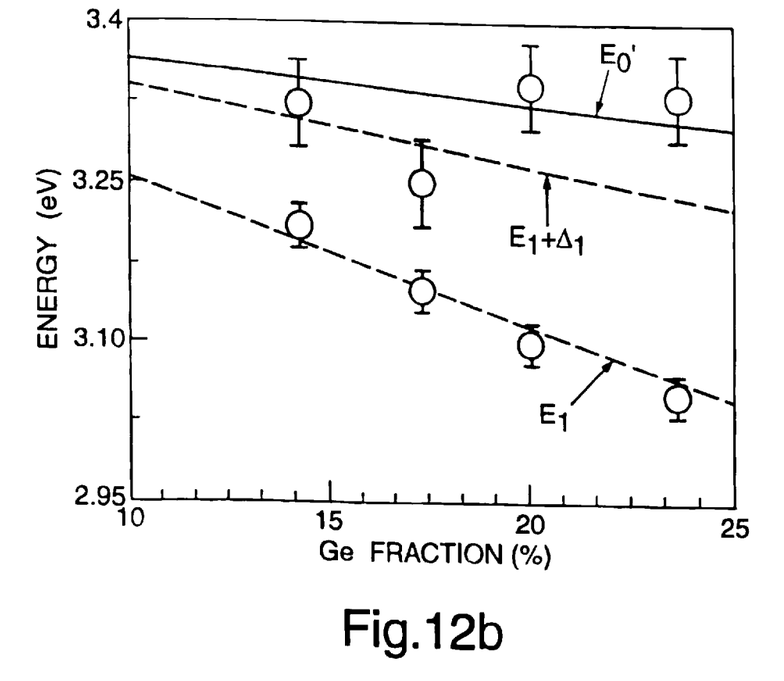

FIG. 12a shows the PSE specta obtained from a Si(cap)/$Si_{0.8}Ge_{0.2}$/Si($p^+$) sample. Differential structure originating from the $E_0{'}$ critical point in the Si cap and from the $E_1$ and $E_1+\Delta_1$ critcal points in the $Si_{0.8}Ge_{0.2}$ alloy are seen. The arrows show the energy positions of the critical points calculated by fitting Lorentzian lineshapes to the measured PSE spectra. Being composition dependent, the energy positions of critical points in alloys such as $Si_{1-x}Ge_x$ allow the alloy compositon, x, to be determined from the PSE spectra. FIG. 12b shows the variation in the energy position of the the $E_1$ and $E_1+\Delta_1$ critcal points for a range of alloy compositions, x, of the $Si_{1-x}Ge_x$ alloy.

Single Wavelength Measurements

The stability in energy position and magnitude of the observed CP structure in the PSE spectra from a sample means that single wavelength PSE measurements made at an energy position where CP structure is observed could be calibrated to yield similar information to the spectroscopic measurements, provided not more than one parameter was being monitored per wavelength of PSE spectra recovered. Superior signal recovery techniques could be used in this case such as phase sensitive detection.

REFERENCES

1) T. Farrell and J. V. Armstrong, Semicond, Sci. Technol 7, 1495 (1992).
2) C. Pickering, Handbook of Crystal Growth (ed D. T. J. Hurle) (Elsevier, Amsterdam) 3, 817 (1994).
3) F. H. Pollak and H. Shen, Mat Sci.Eng.R 20, 275 (1993).
4) A. B. Buckman and N. M. Bashara, J. Optical Society of America 58, 700 (1968).
5) A. B. Buckman, Surface Science 16, 193 (1969).
6) A. B. Buckman, J. Optical Society of America 60, 416 (1970).
7) E. Yang and A. B. Buckman, Phys. Rev. B 5, 2242 (1972).
8) J-Th. Zettler, Th. Dittrich and L. Schrottke, Phys. Stat. Sol. (a) 119, K91 (1990).
9) J-Th. Zettler, H. Mikkelsen, K. Leo, H. Kurz, R. Carlus and A. Forster, Phys. Rev. B 46, 15955 (1992),
10) J.-Th. Zettler, H. Mikkelsen, Th. Trepk and K. Leo, Thin Solid Films 233234, 112 (1993).
11) Y-M. Xiong, P. G. Snyder and J. A. Wooliam, Thin Solid Films 233–234, 399 (1993).
12) Y-M. Xiong, C-C. Wong and T. Saitoh, 1994 International Conference on Solid State Devices and Materials, Yokohama Japan, 205 (1994).
13) Y-M. Xiong C-C. Wong and T. Saitoh, Jpn. J. Appl. Phys. 34 2207 (1995).
14) T. Saitoh, K. Nakamura, H. Hasegawa and Y-M. Xiong, Jpn. J. Appl. Phys. Vol 35, 1696 (1996).
15) R. Vanderhaghen, S. Cueille, B. Drevillon and R. Ossikovski, Phys. Stat Sol (a) 152, 85 (1995).
16) D. J. Robbins, A. J. Pidduck, C. Pickering, I. M. Young and J. L. Glasper, SPIE 1012, 25 (1988).
17) A. Daunois and D. E. Aspnes, Phys. Rev. B 18, 1824 (1972).
18) E. D. Palik (ed), Handbook of Optical Constants, Academic Press (1985).
19) R. T. Carline, C. Pickering D. J. Robbins, W. Y. Leong, A. D. Pitt and A. G. Cullis, Appl. Phys. Lett 64, 1114 (1994).
20) R. T. Carline, C. Pickering, N. S. Garawal, D. Lancefield, L. K. Howard and M. T. Emeny, Presented at SPIE Symposium on Compound Semiconductor Physics and Devices, Sommerset, N.J., USA (1992).

What is claimed is:

1. A method of monitoring material parameters during processing of said material, comprising the steps of:
    modulating the internal electric field of the material,
    monitoring, by using a real-time ellipsometer, derivative spectra that said modulation induces, and
    determining said parameters from said derivative spectra.

2. The method of claim 1 where the derivative spectra are monitored by illuminating the material using an intensity unmodulated probe beam (3).

3. The method of claim 1 where the real time ellipsometer is of the spectroscopic type.

4. The method of claim 3 where the derivative spectra are monitored by dispersing the radiation reflected from the material and by detecting the dispersed radiation by means of a photodetector array.

5. The method of claim 1 where the real time ellipsometer is of the single wavelength type.

6. The method of claim 1 where the internal electric field of the sample is modulated using a charged particle beam.

7. The method of claim 6 where the internal electric field of the sample is modulated using an electron beam.

8. The method of claim 1 where the internal electric field of the sample is modulated using a source of electromagnetic radiation.

9. The method of claim 8 where the internal electric field of the sample is modulated using a laser (8).

10. A method of monitoring material parameters during processing of said material, comprising the steps of modulating the internal electric field of the material, using a real-time ellipsometer to monitor derivative spectra that said modulation induces, and determining said parameters from said derivative spectra, where the internal electric field of the sample is modulated using a laser, where the parameters further include laser power and laser alignment.

11. A method of monitoring material parameters during processing of said material, comprising the steps of modulating the internal electric field of the material, using a real-time ellipsometer to monitor derivative spectra that said modulation induces, and determining said parameters from said derivative spectra, where the derivative spectra is related to one of the material parameters by substituting the values of photo-modulated ellipsometry signal, the third derivative of the dielectric constant and the effective mass into the equations that define Aspne's low field theory.

12. A method of monitoring material parameters during processing of said material, comprising the steps of modulating the internal electric field of the material, using a real-time ellipsometer to monitor derivative spectra that said modulation induces, and determining said parameters from said derivative spectra, where the derivative spectra is related to one of the material parameters by means of the equation:

$$\Delta(\varepsilon_1 + i \cdot \varepsilon_2) = (\eta\theta)^3 \frac{d^3}{dE^3}(\varepsilon_1(E - E_g, \Gamma) + i \cdot \varepsilon_2(E - E_g, \Gamma)) \quad (1)$$

where $\Delta(\in_1 + i.\in_2)$ is the change in the dielectric function E is a spectral energy and $\Gamma$ is a broadness and $(\eta\theta)^3$ is the electro-optic energy given by, $$(\eta\theta)^3 = \frac{q^2\eta^2 F^2}{2\mu} \quad (2)$$

where $\mu$ is the interband effective mass in the direction of the filed, and by substituting the values of photo-modulated ellipsometry signal, the third derivative of the dielectric constant and the effective mass into equations 1 and 2 thereby determining the electric field.

* * * * *